United States Patent [19]

Dietz et al.

[11] Patent Number: 5,302,275

[45] Date of Patent: Apr. 12, 1994

[54] SENSOR ELEMENT FOR AN OXYGEN LIMITING CURRENT PROBE IN ORDER TO DETERMINE THE LAMBDA VALUE OF GAS MIXTURES

[75] Inventors: Hermann Dietz, Gerlingen; Barbara Beyer, Stuttgart; Werner Gruenwald, Gerlingen; Claudio Da La Prieta, Stuttgart, all of Fed. Rep. of Germany

[73] Assignee: Robert Bosch GmbH, Stuttgart, Fed. Rep. of Germany

[21] Appl. No.: 934,489

[22] PCT Filed: Feb. 27, 1991

[86] PCT No.: PCT/DE91/00166

§ 371 Date: Sep. 14, 1992

§ 102(e) Date: Sep. 14, 1992

[87] PCT Pub. No.: WO91/14174

PCT Pub. Date: Sep. 19, 1991

[30] Foreign Application Priority Data

Mar. 13, 1990 [DE] Fed. Rep. of Germany ....... 4007856

[51] Int. Cl.$^5$ ............................................. G01N 27/26
[52] U.S. Cl. .................................... 204/424; 204/425; 204/426; 204/427
[58] Field of Search ............... 204/424, 425, 426, 427, 204/8

[56] References Cited

U.S. PATENT DOCUMENTS

| | | | |
|---|---|---|---|
| 4,579,643 | 4/1986 | Mase et al. | 204/427 |
| 4,645,572 | 2/1987 | Nishizawa et al. | 204/427 |
| 4,647,364 | 3/1987 | Mase et al. | 204/427 |
| 4,670,128 | 6/1987 | Mase et al. | 204/427 |
| 4,728,411 | 3/1988 | Mase et al. | 204/427 |
| 4,755,274 | 7/1988 | Mase et al. | 204/427 |
| 4,839,018 | 6/1989 | Yamada et al. | 204/427 |
| 5,098,549 | 3/1992 | Friese et al. | 204/426 |

FOREIGN PATENT DOCUMENTS

| | | |
|---|---|---|
| 0188900 | 7/1986 | European Pat. Off. . |
| 3703707A1 | 9/1987 | Fed. Rep. of Germany . |
| 3707874A1 | 9/1987 | Fed. Rep. of Germany . |
| 3728618 | 3/1988 | Fed. Rep. of Germany . |
| 3744206A1 | 8/1988 | Fed. Rep. of Germany . |

OTHER PUBLICATIONS

Solid State Ionics 40/41 (1990) 428–432, North–Holland; "Low Temperature Limiting-Current...", Bor Yann Liaw et al.

Primary Examiner—John Niebling
Assistant Examiner—Bruce F. Bell
Attorney, Agent, or Firm—Spencer, Frank & Schneider

[57] ABSTRACT

A sensor element is proposed for an oxygen limiting current probe for the determination of the λ value of gas mixtures, particularly the exhaust gases of internal-combustion engines, whose oxygen supply is provided by a short-circuit cell disposed upstream of the pumping cell of the sensor element. In this way the $CO_2$ and $H_2O$ transverse sensitivity of the sensor element is made ineffective. In order to obtain at the pumping cell a limiting current that is a linear function of the $O_2$ partial pressure, a diffusion barrier must additionally be disposed between the short-circuit cell and the pumping cell.

11 Claims, 1 Drawing Sheet

SENSOR ELEMENT FOR AN OXYGEN LIMITING CURRENT PROBE IN ORDER TO DETERMINE THE LAMBDA VALUE OF GAS MIXTURES

STATE OF THE ART

The invention is based on a sensor element for an oxygen limiting current probe of the type including a pumping cell where oxygen supply is provided by a short-circuit cell disposed upstream of the pumping cell. Such sensor elements, which operate according to the diffusion limiting current principle, measure the diffusion limiting current at a constant voltage applied to the two electrodes of the sensor element. In an oxygen containing measuring gas, this current is a linear function of the oxygen partial pressure as long as the diffusion of the gas to the pumping electrode determines the speed of the reaction taking place. It is known to construct such sensor elements so that the anode as well as the cathode are exposed to the gas to be measured, with the cathode including a diffusion barrier so as to ensure operation within the diffusion limiting current range.

The prior art oxygen limiting current probes generally serve to determine the $\lambda$ value of exhaust gas mixtures from internal-combustion engines. This $\lambda$ value represents the ratio of "total oxygen to the oxygen required for a complete combustion of the fuel" for the air-fuel mixture being combusted in a cylinder.

Due to a simplified and economical manner of manufacturing, the production of sensor elements that can be produced in ceramic sheet and screen-printing technology has become popular in practice in recent years.

Planar sensor elements can be produced in a simple and economical manner from plate or sheet shaped oxygen conducting solid electrolytes, for example of stabilized zirconium dioxide. These sensor elements are coated on both sides with electrodes and leads, namely with an inner pumping electrode on the one side and an outer pumping electrode on the other side. The inner pumping electrode is here advantageously disposed at the end of a diffusion gap or diffusion channel through which measuring gas is able to diffuse in and which serves as a gas diffusion resistance or diffusion barrier.

In addition, German Unexamined Published Patent DE-OS 3,543,759 and EP-A 0,142,992, 0,142,993, 0,188,900 and 0,194,082 disclose sensor elements and detectors which have in common that they each include a pumping cell and a sensing cell composed of plate or sheet shaped oxygen conducting solid electrolytes and two electrodes disposed thereon, and they have a common diffusion gap or diffusion channel.

Finally, DE-OS 3,728,618 discloses a sensor element for polarographic probes for a determination of the $\lambda$ value of gas mixtures. This sensor element includes a plate or sheet shaped solid electrolyte that is conductive for $O^{2-}$ ions and is equipped with outer and inner pumping electrodes, with the inner pumping electrode on the plate or sheet shaped solid electrolyte being disposed in a diffusion channel for the measuring gas. The sensor element further includes conductor paths for the pumping electrodes. At least one second inner pumping electrode is disposed in the diffusion channel on the side facing the inner pumping electrode and this second inner pumping electrode is short-circuited with the first inner pumping electrode.

A lecture by B.Y. Liaw and W. Weppner of the Max-Planck-Institut für Festkörperforschung [Max Planck Institute For Solid State Research] in Stuttgart, held on the occasion of the "7th International Conference on Solid State Ionics," Nov. 5-11, 1989, in Hakone, Japan, disclosed an oxygen limiting current probe based on tetragonal $ZrO_2$ in which a short-circuit cell and an oxidic mixed conductor are attached upstream of an inner pumping electrode (Cathode) for measuring the limiting current. The authors represent the opinion that the upstream connected short-circuit cell and the oxidic mixed conductor simultaneously constitute a diffusion barrier and they expect the oxygen permeation to obey the diffusion laws so that, consequently, it is a linear function of the external oxygen partial pressure and thus generates a limiting current at the subsequently connected pumping cell. However, in fact this is only the case if electrode effects (polarizations) of the short-circuit cell can be neglected and have no influence on the oxygen permeation. Otherwise, no linear relationship is obtained between oxygen partial pressure and measuring signal (pumping current).

The drawbacks of the prior art sensor elements for oxygen current limiting probes, particularly those produced by laminating together a plurality of solid electrolyte sheets, particularly by laminating together sheets based on stabilized $ZrO_2$, are that with increasing pump voltage they exhibit transverse sensitivity to $CO_2$ and $H_2O$. In that case, not only $O_2$ is converted at the inner pumping electrode (cathode), but also $CO_2$ and $H_2O$. The measuring current is considerably greater and no longer a linear function of the oxygen partial pressure.

SUMMARY AND ADVANTAGES

The sensor element according to the invention, which is suitable for a determination of the $\lambda$ value of gas mixtures, particularly of exhaust gases in internal-combustion engines, and which includes a pumping cell where oxygen supply is provided by a short-circuit cell disposed upstream of the pumping cell and a separate diffusion barrier disposed between the short-circuit cell and the pumping cell, has significant advantages compared to the prior art planar sensor elements.

Due to the fact that the sensor element does not receive the oxygen to be measured directly, but by way of an upstream connected short-circuit cell, it is possible, when the sensor element is operated in the exhaust gas of internal-combustion engines, to avoid transverse sensitivity to the other components of the exhaust gas, $CO_2$ and $H_2O$, as it occurs at higher temperatures and higher pump voltages. Additionally, the accumulation of solid particles from the exhaust gas in the diffusion barrier of the probe is prevented so that they are unable to change the diffusion resistance.

Compared to the sensor element presented at the "7th International Conference on Solid State Ionics", the sensor element according to the invention has the advantage that due to the arrangement of a separate diffusion barrier between the pumping cell and the short-circuit cell, the short-circuit cell does not perform the function of a diffusion barrier but merely takes care that the same oxygen partial pressure as in the measuring gas exists upstream of the installed diffusion barrier. The short-circuit cell therefore does not adversely affect the oxygen supply.

The operation of a sensor element according to the invention can be explained as follows:

If in an oxygen concentration cell $O_2$, $Pt/ZrO_2/Pt$, $O_2$, the two Pt electrodes are short-circuited, a short-circuit current will flow until the $O_2$ partial pressure is the same on both sides. If, the gas chamber is limited at least on one side of the cell and is relatively small and the polarizations and ohmic resistances which determine the short-circuit current are correspondingly low, this compensation can take place relatively quickly. In this way, it is possible to transport oxygen from the measuring gas to the actual measuring cell (pumping cell) in a limiting current probe without annoying or damaging exhaust gas components coming in contact with the measuring cell. If, according to the invention, a short-circuit cell is connected upstream of the diffusion barrier and the pumping cell, the short-circuit causes the same $O_2$ partial pressure to be set in the gas chamber upstream of the diffusion barrier as in the exhaust gas.

In the case of the sensor element according to the invention, the pumping cell is thus supplied with oxygen by way of a short-circuit cell disposed upstream of a separate diffusion barrier. A sufficiently large diffusion barrier must then be present between the short-circuit cell and the pumping cell.

According to a first advantageous embodiment of the invention, the sensor element is configured in such a way that the anode of the pumping cell lies within the measuring gas. In this embodiment, the short-circuit cell must replenish all of the oxygen consumed by the measuring current. This oxygen is returned to the measuring gas by way of the anode.

According to a second advantageous embodiment of the invention, the sensor element is configured in such a way that the anode of the pumping cell together with the diffusion barrier and the cathode are disposed in the interior gas chamber of the short-circuit cell. In that case, the oxygen that is generated at the anode of the pumping cell and is consumed at the cathode, is conducted in a gas circuit including the diffusion barrier. The short-circuit cell acts on this gas circuit in a regulating manner only if the $O_2$ partial pressure in the measuring gas changes. It is thus required only to match the $O_2$ partial pressure to the external oxygen partial pressure and not replenish all of the oxygen consumed at the cathode of the pumping cell. In this second embodiment, the adjustment times are generally shorter than in the first embodiment.

Preferably, the sensor elements according to the invention are produced on the basis of plate or sheet shaped ceramic materials which are imprinted, laminated together and sintered according to conventional, known methods, for example screen printing, with the short-circuit cells as well as the pumping cells being obtained in a simple manner by imprinting a plate or sheet shaped solid electrolyte as it is customary for the production of oxygen limiting current probes with a metal belonging to the platinum group.

The diffusion barrier of a sensor element according to the invention is composed of a zone or section of a coarsely porous sintered ceramic material that is permeable to gas to a certain degree and is based, for example, on $Al_2O_3$ or $ZrO_2$, or of a diffusion gap or diffusion channel which, if required, may be filled partially with roughly pre-sintered ceramic material.

BRIEF DESCRIPTION OF THE DRAWINGS

Two advantageous exemplary embodiments of a sensor element according to the invention are shown in the drawing figures in a simplified manner.

DETAILED DESCRIPTION OF THE PREFERRED EMBODIMENT

Figure 1:
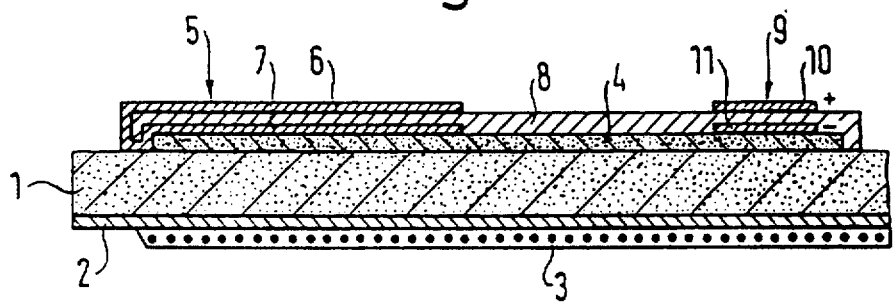
FIG. 1 is a schematic longitudinal sectional view of the front portion of a first embodiment of the sensor element according to the invention.

The first embodiment of the sensor element according to the invention shown schematically in FIG. 1 is composed of a carrier or substrate 1 in the form of a small plate on whose one side is disposed an insulation layer 2 and a heater 3 and on whose other side a diffusion barrier 4 as well as a short-circuit cell 5 composed of electrodes 6 and 7 as well as a solid electrolyte layer 8 and a pumping cell 9 composed of an anode 10, a cathode 11 and a solid electrolyte layer 8.

The carrier or substrate 1 of the sensor element according to the invention is composed of a ceramic material as it is customarily employed for the production of sensor elements, for example on the basis of $ZrO_2$ or $Al_2O_3$. It has been found to be advantageous to produce the sensor element of sheets made of an unsintered ceramic material having a layer thickness of 0.3 to 2.0 mm, particularly of about 0.6 to 1.0 mm.

Insulation layer 2 is composed of a conventional insulating layer, for example based on $Al_2O_3$. It may have a thickness of, for example, 15 to 20 $\mu$m. The heater 3 may be, for example, a heater based on $Pt/Al_2O_3$ which can be obtained by printing on an appropriate cermet paste.

The diffusion barrier 4 is composed of a coarsely porous sintering ceramic material, for example based on $Al_2O_3$ or $ZrO_2$, that can be obtained by imprinting a corresponding paste or laminating on a porously sintering sheet. Its layer thickness is advantageously about 20 to 50 $\mu$m. As shown in FIG. 1, it need not fill the entire area. It is sufficient if parts of the oxygen diffusion path between the short-circuit cell anode and the pumping cell cathode are constricted by a barrier.

The porosity of the diffusion barrier may be varied, if required, by the addition of pore formers which combust during the sintering process, decompose or evaporate. Typical pore formers that can be employed are, for example, thermal soot powder, graphite carbon; plastics, for example based on polyurethane; salts, for example ammonium carbonate; and further organic substances such as, for example, theobromine and indanthrone. Such pore formers may be added to the porously sintering starting material in various quantities.

The electrodes of short-circuit cell 5 and of pumping cell 9 are preferably composed of a metal of the platinum group, particularly platinum, or of alloys of metals of the platinum group or alloys of metals of the platinum group with other metals. If required, they contain a ceramic supporting frame material, for example in the form of a YSZ powder, at a volume percentage of preferably about 40 volume percent. They are porous and as thin as possible. Preferably they have a thickness of 8 to 15 $\mu$m. The conductor paths belonging to the electrodes are preferably also composed of platinum or a platinum alloy of the described type. Moreover, they may likewise be produced from a paste based on a noble metal cermet.

Solid electrolyte layer 8 is composed of one of the known oxides of four-valent metals employed for the production of $O^{2-}$ ion conducting solid electrolyte sheets, such as, in particular, $ZrO_2$, $CeO_2$, $HfO_2$ and $ThO_2$ containing two-valent earth alkali oxides and/or preferably three-valent oxides of the rare earths. Typically, the layer may be composed of approximately 50 to 97 mole percent $ZrO_2$, $CeO_2$, $HfO_2$ or $ThO_2$ and 50 to 3 mole percent CaO, MgO or SrO and/or oxides of the rare earths and particularly $Y_2O_3$. Advantageously, the layer is composed of $ZrO_2$ that is stabilized with $Y_2O_3$. The thickness of the layer may advantageously lie at 10 to 200 $\mu$m, particularly 15 to 50 $\mu$m.

In the case of this first embodiment, anode 10 lies in the measuring gas and the short-circuit cell replenishes all of the oxygen consumed by the measuring current. Thus the oxygen of the measuring gas penetrates electrolyte layer 8 in the form of ionized oxygen which is developed at the second electrode (anode of the short-circuit cell) 7 back into oxygen ($O_2$). This oxygen penetrates the diffusion barrier and is pumped off by the cathode 11 of pumping cell 9 and discharged to the measuring gas by way of pumping cell anode 10.

Figure 2:
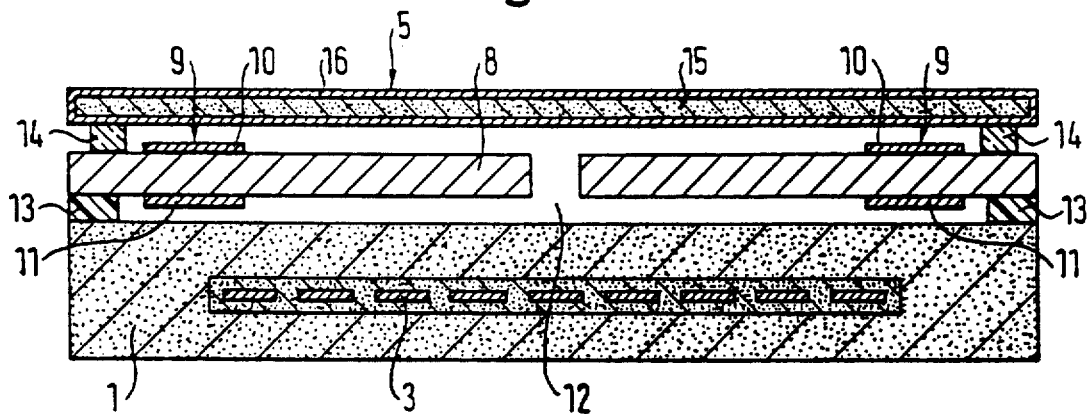
FIG. 2 is a schematic cross-sectional view of a second embodiment of the sensor element according to the invention.

In the case of the second advantageous embodiment of the sensor element according to the invention, shown schematically in FIG. 2, the anode 10 of pumping cell 9 is disposed in the interior gas chamber of short-circuit cell 5.

The sensor element is composed of the carrier or substrate 1 of ceramic material, for example, a $ZrO_2$ ceramic, and includes a heater 3 that is embedded in an insulating layer, a diffusion gap 12, which in the case of this second embodiment forms the diffusion barrier, an annular pumping cell 9 equipped with an anode 10 and a cathode 11 as well as a solid electrolyte layer 8, a sealing frame 13, glass fittings 14 and a short-circuit cell 5 composed of a solid electrolyte sheet or a small solid electrolyte plate 15, for example of a $ZrO_2$ ceramic, which is covered all around by electrodes 16.

Glass fittings 14 which determine the distance of short-circuit cell 5 from pumping cell 9 may be composed, for example, of a high melting point glass and may have such dimensions that the distance of the electrode of short-circuit cell 5 facing pumping cell 9 from the anode 10 of pumping cell 9 is about 20 to 500 $\mu$m.

The element may be produced by printing, laminating together and sintering of appropriate sheets, with the diffusion gap possibly being produced, for example, by imprinting a coating substance which decomposes, evaporates or combusts without residue at the pre-sintering or sintering temperature. If required, however, diffusion gap 12 may also be filled with a coarsely porous sintering ceramic material, for example based on $Al_2O_3$ or $ZrO_2$. In this process, short-circuit cell 5 and pumping cell 9 and its carrier 1 are sintered separately and then connected by fittings 14.

In the case of this sensor element 1 with a fixed-on short-circuit cell 5, the oxygen developed at anode 10 of pumping cell 9 and consumed at cathode 11 is conducted in a gas circuit over the diffusion barrier, and the short-circuit cell enters the gas circuit only in a regulating manner if the $O_2$ partial pressure in the measuring gas changes.

The production of a sensor element according to the invention may be effected by machine in a multiple access process. The elements may be inserted in a housing of a customary, known type and may be employed to determine the $\lambda$ value of gas mixtures. The short-circuit cell connected upstream then avoids $CO_2$ and $H_2O$ transverse sensitivity as it is customary in comparable sensor elements. The upstream connected short-circuit cell additionally prevents solid particles from the exhaust gas from being deposited in the diffusion barrier of the probe to thus change the diffusion resistance.

We claim:

1. A sensor element for determining the $\lambda$ value of gas mixtures, said element comprising a pumping cell as the measuring cell, said pumping cell having a cathode; a short-circuit cell which precedes the pumping cell on the side of the measuring gas and which provides the sole access to the pumping cell for the measuring gas; and a diffusion barrier disposed between said short-circuit cell and said cathode of said pumping cell.

2. A sensor element according to claim 1, produced in ceramic sheet technology.

3. A sensor element according to claim 1, wherein said pumping cell has an anode which lies within an interior gas chamber of said short-circuit cell.

4. A sensor element for determining the $\lambda$ value of gas mixtures, said element comprising: a pumping cell as the measuring cell; a short-circuit cell arranged upstream of said pumping cell for supplying oxygen to said pumping cell; and, a separate diffusion barrier disposed between said short-circuit cell and said pumping cell.

5. A sensor element according to claim 4, produced in ceramic sheet technology.

6. A sensor element according to claim 4, wherein said pumping cell has an anode which lies within an interior gas chamber of said short-circuit cell.

7. A sensor element according to claim 4, wherein said pumping cell has an anode which lies in the measuring gas.

8. A sensor element according to claim 4, further comprising a plate-shaped carrier having on one side an insulating layer and a heater and on its other side said short-circuit cell and said pumping cell, said cells being separated from one another by said separate diffusion barrier.

9. A sensor element according to claim 5, further comprising:
   a plate shaped carrier of a ceramic material;
   a sealing frame member of an insulation material disposed on a surface of said carrier and extending along its peripheral edge;
   a plate of solid electrolyte material disposed on said frame member, with said plate having a central gap which forms said diffusion barrier;
   first and second annular electrodes disposed opposite one another on opposite respective first and second surfaces of said plate of electrolyte material to form an annular said pumping cell, with said first electrode facing said carrier and being spaced from said surface of said carrier and said second electrode being a cathode; and
   wherein said short circuit cell comprises a layer of solid electrolyte covered on all surfaces by a conductive material and disposed over said second electrode and said second surface of said plate of solid electrolyte and spaced therefrom by glass fittings to define an inner gas chamber for said short-circuit cell.

10. A sensor element according to claim 8, wherein: said diffusion barrier comprises a layer of a coarsely porous sintered ceramic material disposed on said other side of said carrier; one electrode of said pumping cell and one electrode of said short-circuit cell are disposed on said diffusion barrier layer in a spaced relationship; a layer of a solid electrolyte material is disposed on said barrier layer, said one electrode of said pumping cell and said one electrode of said short-circuit cell; and the other electrode of said pumping cell and the other electrode of said short-circuit cell are disposed on said layer of solid electrolyte material overlying the associated said one electrode, with said one electrode and said other electrode of said short circuit cell being conductively connected together.

11. A sensor element according to claim 10, wherein said other electrode of said pumping cell is a cathode of said pumping cell.

* * * * *